United States Patent
Lan

(10) Patent No.: US 9,963,471 B2
(45) Date of Patent: May 8, 2018

(54) LIQUID CRYSTAL VERTICAL ALIGNMENT AGENT, LIQUID CRYSTAL DISPLAY ELEMENT AND MANUFACTURE METHOD OF LIQUID CRYSTAL DISPLAY ELEMENT

(71) Applicant: Shenzhen China Star Optoelectronics Technology Co., Ltd., Shenzhen, Guangdong (CN)

(72) Inventor: Song Lan, Guangdong (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 284 days.

(21) Appl. No.: 14/784,727

(22) PCT Filed: Jun. 26, 2015

(86) PCT No.: PCT/CN2015/082510
§ 371 (c)(1),
(2) Date: Oct. 15, 2015

(87) PCT Pub. No.: WO2016/201720
PCT Pub. Date: Dec. 22, 2016

(65) Prior Publication Data
US 2017/0158715 A1    Jun. 8, 2017

(30) Foreign Application Priority Data

Jun. 18, 2015   (CN) .......................... 2015 1 0341139

(51) Int. Cl.
*C09K 19/00*   (2006.01)
*C07F 7/18*   (2006.01)
(Continued)

(52) U.S. Cl.
CPC .......... *C07F 7/1856* (2013.01); *C07F 7/1836* (2013.01); *C07F 7/1852* (2013.01);
(Continued)

(58) Field of Classification Search
CPC .... C07F 7/1856; C07F 7/1836; C07F 7/1852; C09K 19/56; G02F 1/133771;
(Continued)

(56) References Cited

U.S. PATENT DOCUMENTS

2003/0211342 A1* 11/2003 Nomura .................. C03C 17/42
428/447
2011/0118422 A1* 5/2011 Akiike .................... C08G 77/08
525/431
2012/0249940 A1* 10/2012 Choi .................. G02F 1/133753
349/123

* cited by examiner

*Primary Examiner* — Ruiyun Zhang
(74) *Attorney, Agent, or Firm* — Andrew C. Cheng

(57) ABSTRACT

The present invention provides a liquid crystal vertical alignment agent, and the liquid crystal vertical alignment agent can make the liquid crystal molecules vertically orientated relative to the substrate surface. The liquid crystal vertical alignment agent makes a cheap price, a stable performance and can make the liquid crystal molecules be vertically aligned. The alignment film such as polyimide (PI) in the present liquid crystal display (such as TFT-LCD) can be replaced, which is beneficial for raising the display performance of the liquid crystal display. The present invention further provides a liquid crystal display element, and the liquid crystal display element utilizes the said liquid crystal vertical alignment agent to make the alignment of the liquid crystal molecules in the vertical direction more consistent and have long term stability.

10 Claims, 1 Drawing Sheet

A: head group   B: middle base group   C: tail group

(51) Int. Cl.
*C09K 19/56* (2006.01)
*G02F 1/1337* (2006.01)
*G02F 1/1341* (2006.01)

(52) U.S. Cl.
CPC ............ *C09K 19/56* (2013.01); *G02F 1/1341* (2013.01); *G02F 1/133711* (2013.01); *G02F 1/133788* (2013.01); *G02F 2001/13415* (2013.01); *G02F 2001/133742* (2013.01); *Y10T 428/10* (2015.01); *Y10T 428/1005* (2015.01)

(58) Field of Classification Search
CPC ............. G02F 1/133788; G02F 1/1341; G02F 2001/133765; G02F 2001/133742; Y10T 428/10; Y10T 428/1005; Y10T 428/1009; Y10T 428/1014
USPC ......... 428/1.1, 1.2, 1.21, 1.23; 349/123, 131
See application file for complete search history.

A: head group  B: middle base group  C: tail group

LIQUID CRYSTAL VERTICAL ALIGNMENT AGENT, LIQUID CRYSTAL DISPLAY ELEMENT AND MANUFACTURE METHOD OF LIQUID CRYSTAL DISPLAY ELEMENT

CROSS REFERENCE

This application claims the priority of Chinese Patent Application No. 201510341139.7, entitled "Liquid crystal vertical alignment agent, liquid crystal display element and manufacture method of liquid crystal display element", filed on Jun. 18, 2015, the disclosure of which is incorporated herein by reference in its entirety.

FIELD OF THE INVENTION

The present invention relates to a display technology field, and more particularly to a liquid crystal vertical alignment agent, a liquid crystal display element and a manufacture method of the liquid crystal display element.

BACKGROUND OF THE INVENTION

Recently, the liquid crystal display (LCD) technology has become popular because of the unique advantages of low power consumption, low radiation, light weight and convenience. For obtaining the fine display result for the liquid crystal display, the liquid crystal molecules demand great initial alignment (initial orientation).

For orientating the liquid crystal molecules in a certain direction relative to the substrate surface, the liquid crystal alignment films are arranged on the substrate surfaces. The vertical alignment liquid crystal display has excellent performances of higher contrast, fast response speed and etc. The liquid crystal vertical orientation technology has been widely utilized. Generally, the vertical alignment liquid crystal display according to prior art uses the polyimide (PI) with alkyl side chain or polyamic acid thin film to be the alignment film. The common PI alignment film materials can be the rubbing alignment type PI material and light alignment type PI material. The rubbing alignment type PI material can easily generates the powder, the static electricity and the circuit damage of the liquid crystal display element in the rubbing procedure; the light alignment type PI material can prevent the static electricity and the powder. However, with the restriction of the property of the PI material itself, the heating resistance and the aging resistance of the alignment film is bad and the hygroscopicity is higher. In the storage and delivery, the deterioration can easily occur and results in the uneven orientation of the liquid crystals. Meanwhile, the ability of PI anchoring the liquid crystal molecules is weaker, and thus influences the quality of the panel. More significantly, the price of PI material is expensive, and the process of film formation is complicated, which causes the panel cost is raised.

Therefore, there is a need to provide a liquid crystal vertical alignment agent, a liquid crystal display element and a manufacture method of the liquid crystal display element which make a cheap price, stable performance and can make the liquid crystal molecules vertically aligned while eliminating the PI alignment film.

SUMMARY OF THE INVENTION

On this account, the embodiment of the present invention first provides a liquid crystal vertical alignment agent to replace the use of the polyimide (PI) alignment films according to prior art. The liquid crystal vertical alignment agent makes a cheap price, a stable performance and can make the liquid crystal molecules be vertically aligned.

First, the present invention provides a liquid crystal vertical alignment agent, and a molecular formula of the liquid crystal vertical alignment agent is represented by $R_2Si\text{—}(OR_1)_3$, wherein $R_1$ is $\text{—}Si(CH_3)_3$, an alkyl group of which a number of H atom or carbon atom is 1-5, and $R_2$ is a structure of the following equation (E):

in equation (E), $B_1$ is single chain, —$CH_2$— or —$(CH_2)_2$—, $B_2$ is —O—, —COO—*, —OCO—* or —NHCO—*, wherein the * of $B_2$ is linked at one side of $B_3$, and $B_3$ is phenylene alkylene of which a number of carbon atoms is 2-6, alkylene containing olefinic bond or acetylene bond of which a number of carbon atoms is 3-8, and $B_4$ is —O—, —(CO)NH—*, —COO—* or —OCO—*, wherein the * of $B_4$ is linked at one side of C, and C is linear alkylbenzene of which a number of carbon atoms is 1-10.

In the embodiment of the present invention, $R_1$ is —$CH_3$, —$Si(CH_3)_3$ or —$CH_2CH_3$.

In the embodiment of the present invention, the $B_3$ is —$C_6H_4$—, alkylene of which a number of carbon atoms is 2-6, —CH=CH— or —$(CH_3)C$=$C(CH_3)$—.

In the embodiment of the present invention, the C is linear alkylbenzene of which a number of carbon atoms is 5-8.

First, the present invention provides a small molecule vertical alignment agent which can make the liquid crystal molecules vertically orientated relative to the substrate surface. The anchoring function to the liquid crystal molecules is stronger and the alignment film such as polyimide (PI) in the present liquid crystal display (such as TFT-LCD) can be replaced. The liquid crystal vertical alignment agent makes a cheap price, a stable performance and can make the liquid crystal molecules be vertically aligned.

Second, the present invention provides a liquid crystal display element, and the liquid crystal display element comprises a liquid crystal display element precursor, and the liquid crystal display element precursor comprises two substrates, which are oppositely positioned and have conductive films, and a liquid crystal medium positioned between the substrates, and the liquid crystal medium comprises a liquid crystal vertical alignment agent, liquid crystals and a photopolymerization monomer (in short of RM), wherein surfaces of the substrates do not comprises liquid crystal alignment films, and the liquid crystal vertical alignment agent is employed to make the liquid crystals vertically orientated on the surfaces of the substrates in an initial state, and the liquid crystal display element precursor is employed to be irradiated with ultraviolet light to form the liquid crystal display element in a state of being applied with voltages, wherein a molecular formula of the liquid crystal vertical alignment agent is represented by $R_2Si\text{—}(OR_1)_3$, and $R_1\text{—}Si(CH_3)_3$, an alkyl group of which a number of H atom or carbon atom is 1-5, and $R_2$ is a structure of the following equation (E):

in equation (E), $B_1$ is single chain, —$CH_2$— or —$(CH_2)_2$—, $B_2$ is —O—, —COO—*, —OCO—* or —NHCO—*, wherein the * of $B_2$ is linked at one side of $B_3$, and $B_3$ is phenylene, alkylene of which a number of carbon atoms is 2-6, alkylene containing olefinic bond or acetylene bond of which a number of carbon atoms is 3-8, and $B_4$ is —O—, —(CO)NH—*, —COO—* or —OCO—*, wherein the * of $B_4$ is linked at one side of C, and C is linear alkylbenzene of which a number of carbon atoms is 1-10.

In the embodiment of the present invention, a mass ratio of the liquid crystal vertical alignment agent in the liquid crystal medium is 0.1%-5%.

In the embodiment of the present invention, a mass ratio of the photopolymerization monomer RM in the liquid crystal medium is 0.01%-0.1%.

In the embodiment of the present invention, the photopolymerization monomer RM is

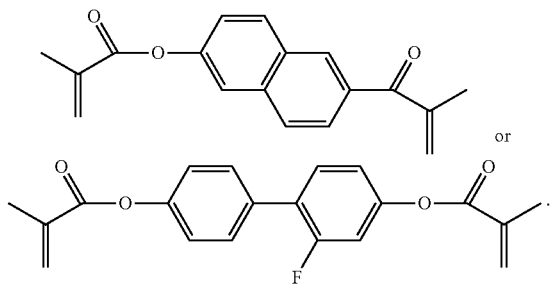

Before the liquid crystal display element provided by the present invention is applied with voltages and irradiated with ultraviolet light, the liquid crystal vertical alignment agent is employed to make the liquid crystals vertically orientated on the surfaces of the substrates in an initial state. The initial alignment directions of the whole liquid crystals are more consistent. After an appropriate voltage is applied thereto, the liquid crystal molecules will be twisted. Then, after irradiation of ultraviolet light with a certain energy to make the photopolymerization monomer RM be polymerized and deposed on the surface of the substrate to realize the objective of anchoring liquid crystals (in short of LC); after the applied voltage is removed, the LC molecules generates a certain twisted angle to obtain the liquid crystal display element.

The liquid crystal display element provided by the present invention utilizes the said liquid crystal vertical alignment agent to make the alignment of the liquid crystal molecules in the vertical direction more consistent and have long term stability. Thus, the response speed of the liquid crystal display element is faster to show the great electrical property, transmission and contrast. The image display performance is excellent.

Third, the present invention provides a manufacture method of a liquid crystal display element, comprising steps of:

(1) adding a liquid crystal vertical alignment agent in liquid crystals containing a photopolymerization monomer to obtain a liquid crystal medium, and a molecular formula of the vertical alignment agent is represented by $R_2Si$—$(OR_1)_3$, wherein $R_1$ is —$Si(CH_3)_3$, an alkyl group of which a number of H atom or carbon atom is 1-5, and $R_2$ is a structure of the following equation (E):

$$-B_1-B_2-B_3-B_4-C \quad (E),$$

in equation (E), $B_1$ is single chain, —$CH_2$— or —$(CH_2)_2$—, $B_2$ is —O—, —COO—*, —OCO—* or —NHCO—*, wherein the * of $B_2$ is linked at one side of $B_3$, and $B_3$ is phenylene, alkylene of which a number of carbon atoms is 2-6, alkylene containing olefinic bond or acetylene bond of which a number of carbon atoms is 3-8, and $B_4$ is —O—, —(CO)NH—*, —COO—* or —OCO—*, wherein the * of $B_4$ is linked at one side of C, and C is linear alkylbenzene of which a number of carbon atoms is 1-10;

(2) adding the aforesaid liquid crystal medium between two substrates, which are oppositely positioned and have conductive films to obtain a liquid crystal display element precursor, wherein surfaces of the substrates do not comprises liquid crystal alignment films;

(3) irradiating the liquid crystal display element precursor with ultraviolet light to form the liquid crystal display element in a state of being applied with voltages.

In the embodiment of the present invention, in the step (2), the liquid crystal medium is injected between the substrates having conductive films with a one drop filling process.

The manufacture method of the liquid crystal display element provided by the embodiment of the present invention makes the manufacture process simple, and strong operation operability to replace the manufacture of the alignment film such as polyimide (PI) in the present liquid crystal display element (such as TFT-LCD). It can significantly simplify the manufacture flow of the liquid crystal display element to reduce the production cost, and raise the display performance of the liquid crystal display element.

DETAILED DESCRIPTION OF PREFERRED EMBODIMENTS

Figure 1:
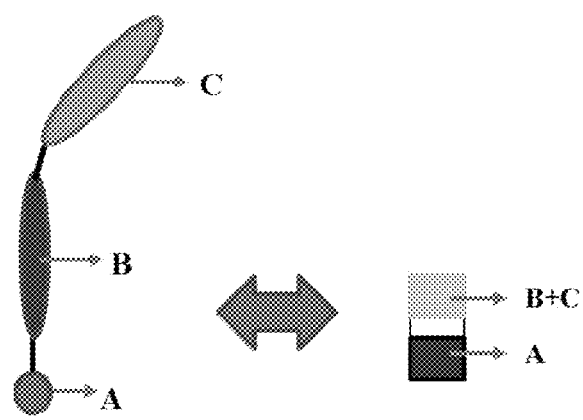
FIG. 1 is a structure diagram of a liquid crystal display vertical alignment agent in the embodiment of the present invention.

Embodiments of the present invention are described in detail with the technical matters, structural features, achieved objects, and effects with reference to the accompanying drawings as follows. It is clear that the described embodiments are part of embodiments of the present invention, but not all embodiments. Based on the embodiments of the present invention, all other embodiments to those of ordinary skill in the premise of no creative efforts obtained, should be considered within the scope of protection of the present invention. It should be noted that the specific embodiments described herein are merely for explaining the preset invention and are not intended to limit the present invention.

First, the present invention provides a liquid crystal vertical alignment agent, and a molecular formula of the liquid crystal vertical alignment agent is represented by $R_2Si$—$(OR_1)_3$, wherein $R_1$ is —$Si(CH_3)_3$, an alkyl group of which a number of H atom or carbon atom is 1-5, and $R_2$ is a structure of the following equation (E):

$$-B_1-B_2-B_3-B_4-C \quad (E),$$

in equation (E), $B_1$ is single chain, —$CH_2$— or —$(CH_2)_2$—, $B_2$ is —O—, —COO—*, —OCO—* or —NHCO—*, wherein the * of $B_2$ is linked at one side of $B_3$, and $B_3$ is phenylene, alkylene of which a number of carbon atoms is 2-6, alkylene containing olefinic bond or acetylene bond of which a number of carbon atoms is 3-8, and $B_4$ is —O—, —(CO)NH—*, —COO—* or —OCO—*, wherein the * of $B_4$ is linked at one side of C, and C is linear alkylbenzene of which a number of carbon atoms is 1-10.

In the embodiment of the present invention, $R_1$ is linear alkyl or branched alkyl of which a number of carbon atoms is 1-5.

In the embodiment of the present invention, $R_1$ is —$CH_3$, —$Si(CH_3)_3$ or —$CH_2CH_3$.

In the embodiment of the present invention, the $B_3$ is —$C_6H_4$—, liner alkylidene radical of which a number of carbon atoms is 2-6, —CH=CH— or —$(CH_3)C=C(CH_3)$—.

In the preferred embodiment of the present invention, the C is linear alkylbenzene of which a number of carbon atoms is 5-8.
Specifically, the following simple and illustrative structures, which may eliminate some compounds, such as C (linear alkylbenzene), can be illustrated for the liquid crystal vertical alignment agent but not limited to these:
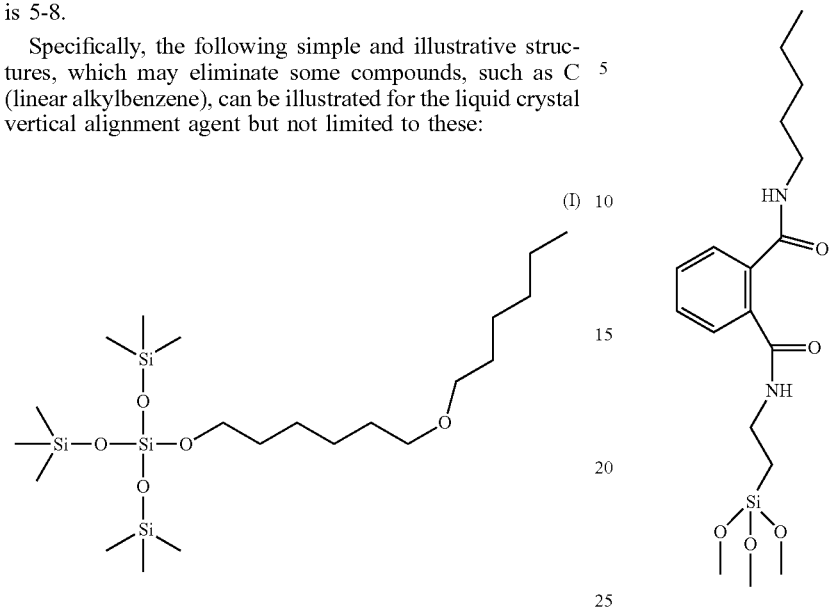
(I)
(II)
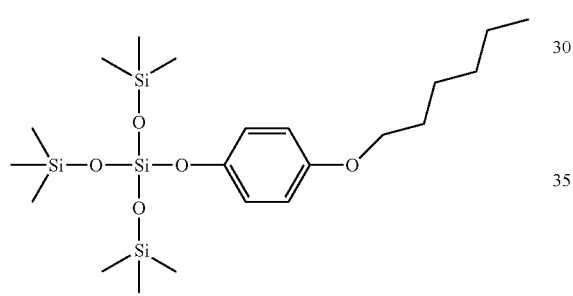
(III)
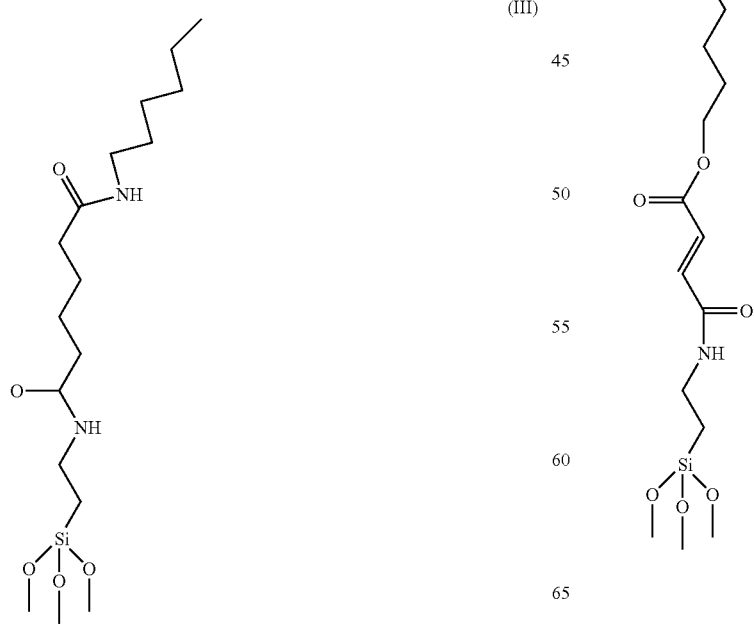
(IV)
(V)

(VI)

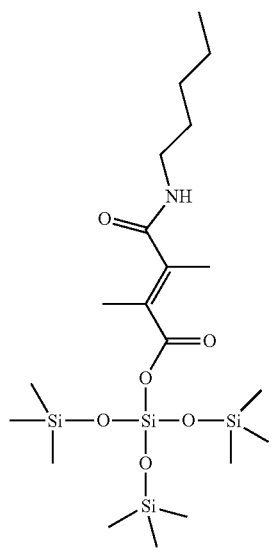

The compound represented by $R_2Si-(OR_1)_3$ can be obtained by organic synthesis.

AS being a specific synthesis embodiment, several synthetic routes of the liquid crystal vertical alignment agent represented by $R_2Si-(OR_1)_3$ can be illustrated:

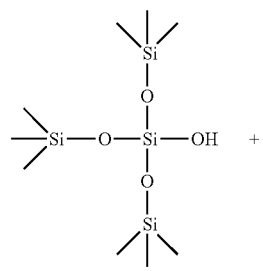

Tris(Trimethylsilyloxy)silanol

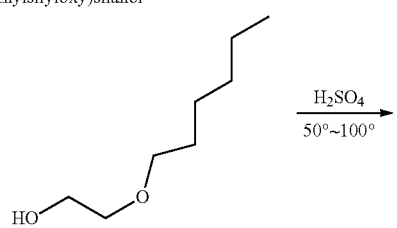

Ethylene Glycol Monohexyl Ether

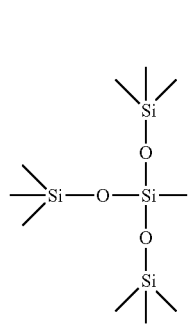

The specific synthesis process of the compound (I):

the H1-NMR data of the compound (I) is below: δ (ppm): 0.08 (27H), 3.96 (2H), 3.56 (2H), 3.37 (2H), 1.46 (2H), 1.29 (4H), 1.33 (2H), 0.96 (3H).

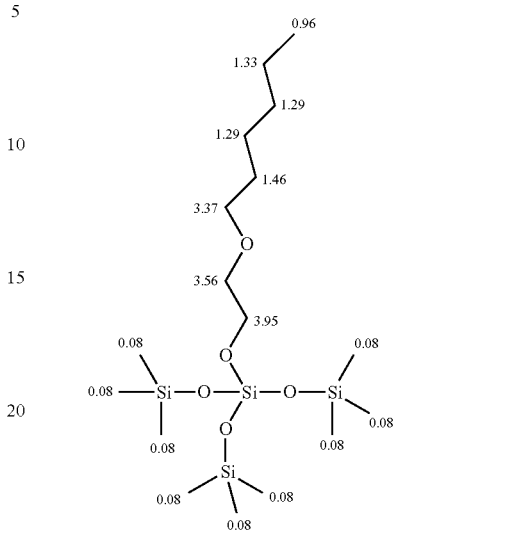

In the embodiment of the present invention, the synthesis of the liquid crystal vertical alignment agent as shown in (II) is similar with the synthesis of the liquid crystal vertical alignment agent as shown in (I).

In the embodiment of the present invention, the synthesis of the liquid crystal vertical alignment agent as shown in (III) is similar with the synthesis of the liquid crystal vertical alignment agent as shown in (IV).

The specific synthesis process of the compound (IV):

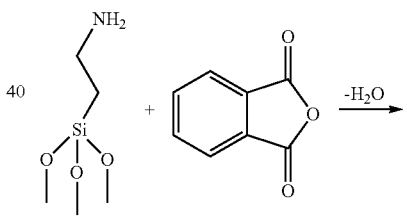

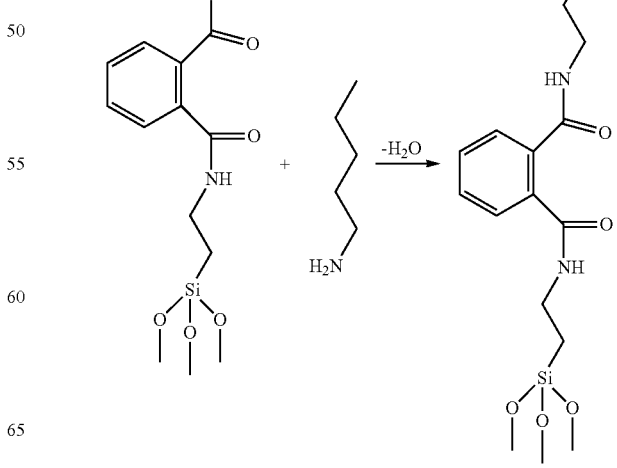

the H1-NMR data of the compound (IV) is below: δ (ppm): 0.96 (3H), 1.33 (2H), 1.29 (2H), 1.59 (2H), 3.20 (2H), 8.0 (1H), 8.13 (2H), 7.69 (2H), 3.55 (9H), 3.2 (2H).
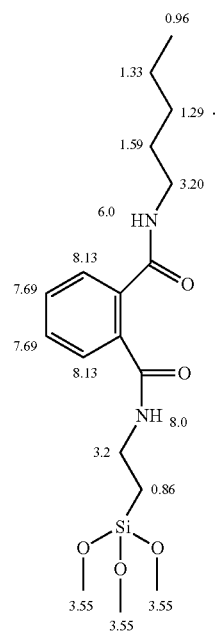 [SMILES: CCCCCNC(=O)c1ccccc1C(=O)NCC[Si](OC)(OC)OC]
The specific synthesis process of the compound (V) is below:
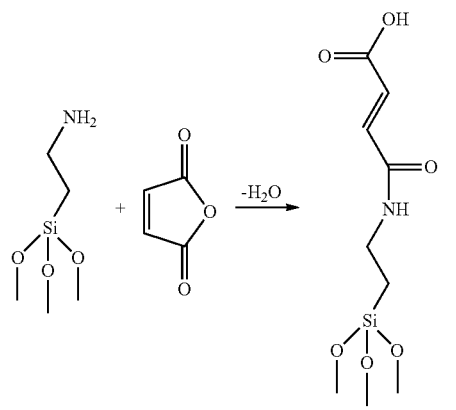
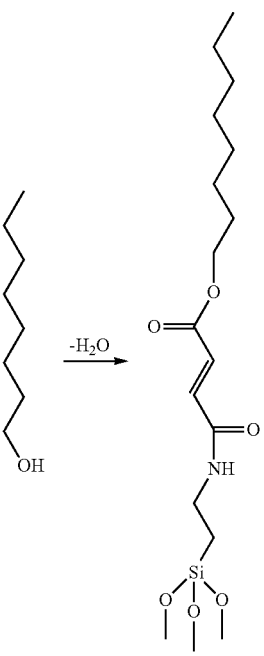
the H1-NMR data of the compound (V) is below: δ (ppm): 0.96 (3H), 1.33 (2H), 1.29 (8H), 1.57 (2H), 4.15 (2H), 3.55 (9H), 8.0 (1H), 3.0 (2H), 0.84 (2H), 7.49 (1H).
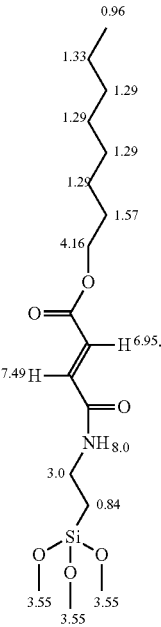 [SMILES: CCCCCCCCOC(=O)/C=C/C(=O)NCC[Si](OC)(OC)OC]

The specific synthesis process of the compound (IV):

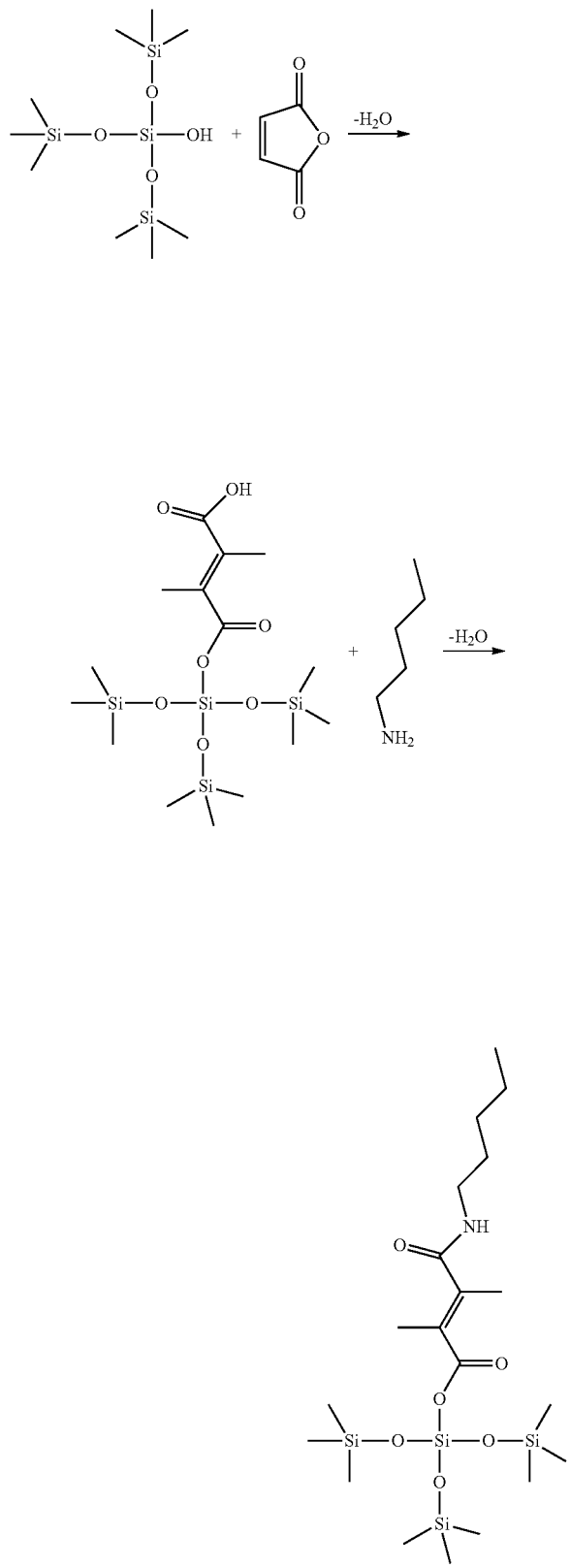

the H1-NMR data of the compound (IV) is below:

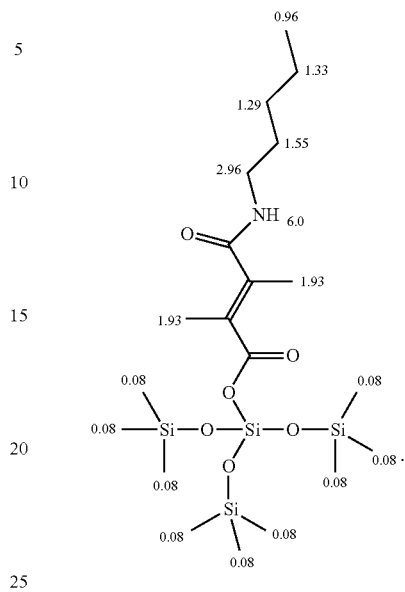

In the liquid crystal vertical alignment agent provided by the embodiment of the present invention, a head group A, a middle base group B and a tail group C (as shown in FIG. 1), wherein the head group A is $Si(OR_1)_3$—, and the head group is a polar alloy group, which mainly functions to anchor the liquid crystal vertical alignment agent on the substrate surface of the liquid crystal display but the difference of the substrate material can result in the different basic function mechanisms: 1, the function with the ITO conductive film on the substrate (or the electrode) is to use the lone pair electrons on the oxygen atom in —Si—O— and the empty p orbit and d orbit hybridization in the indium atom (the configuration of extra-nuclear electron: In:[Kr] $4d^{10}5s^25p^1$) or the stannum atom (the configuration of extra-nuclear electron: Sn:[Kr]$4d^{10}5s^25p^2$) in the ITO on the substrate surface to be combined in a way of coordinate bond; 2, the function mechanism with the SiNx protective film on the substrate is to use the oxygen atom in —Si—O— and the nitride atom in the SiNx to generate the intermolecular force; and the main functions of the middle base group and the tail group is similar to the function of the PI branch chain to make the liquid crystal molecules vertically aligned in a way of steric hindrance. The flexible tail group of the liquid crystal vertical alignment agent can induce the long axis of the liquid crystal molecule vertically aligned with the substrate.

All the time, the function of the head group A is to anchor with the substrate surface. The functions of the middle base group B and the tail group C is to make the LC vertically orientated with the substrate in the way of steric hindrance.

The small molecule liquid crystal vertical alignment agent provided by the present invention can make the liquid crystal molecules vertically orientated relative to the substrate surface. The anchoring function to the liquid crystal molecules is stronger and the alignment film such as polyimide (PI) in the present liquid crystal display (such as TFT-LCD) can be replaced, which can significantly simplifies the manufacture flow of the liquid crystal display element to reduce the production cost, and raise the display performance of the liquid crystal display element.

Second, the present invention provides a liquid crystal display element. The liquid crystal display element comprises a liquid crystal display element precursor, and the liquid crystal display element precursor comprises two substrates, which are oppositely positioned and have conductive films, and a liquid crystal medium positioned between the substrates, and the liquid crystal medium comprises a liquid crystal vertical alignment agent, liquid crystals and a photopolymerization monomer RM, wherein surfaces of the substrates do not comprises liquid crystal alignment films, and the liquid crystal vertical alignment agent is employed to make the liquid crystals vertically orientated on the surfaces of the substrates in an initial state, and the liquid crystal display element precursor is employed to be irradiated with ultraviolet light to form the liquid crystal display element in a state of being applied with voltages, wherein a molecular formula of the liquid crystal vertical alignment agent is represented by $R_2Si-(OR_1)_3$, and $R_1$ is $-Si(CH_3)_3$, an alkyl group of which a number of H atom or carbon atom is 1-5, and $R_2$ is a structure of the following equation (E):

$$-B_1-B_2-B_3-B_4-C \qquad (E),$$

in equation (E), $B_1$ is single chain, $-CH_2-$ or $-(CH_2)_2-$, $B_2$ is $-O-$, $-COO-*$, $-OCO-*$ or $-NHCO-*$, wherein the * of $B_2$ is linked at one side of $B_3$, and $B_3$ is phenylene, alkylene of which a number of carbon atoms is 2-6, alkylene containing olefinic bond or acetylene bond of which a number of carbon atoms is 3-8, and $B_4$ is $-O-$, $-(CO)NH-*$, $-COO-*$ or $-OCO-*$, wherein the * of $B_4$ is linked at one side of C, and C is linear alkylbenzene of which a number of carbon atoms is 1-10.

In the embodiment of the present invention, $R_1$ is linear alkyl or branched alkyl of which a number of carbon atoms is 1-5.

In the embodiment of the present invention, $R_1$ is $-CH_3$, $-Si(CH_3)_3$ or $-CH_2CH_3$.

In the embodiment of the present invention, the $B_3$ is $-C_6H_4-$, liner alkylidene radical of which a number of carbon atoms is 2-6, $-CH=CH-$ or $-(CH_3)C=C(CH_3)-$.

In the preferred embodiment of the present invention, the C is linear alkylbenzene of which a number of carbon atoms is 5-8.

The liquid crystal display element provided by the present invention is shown in FIG. 2(a)-(d), and an ITO electrode on the entire surface is formed on the upper side of the substrate, and the ITO electrode with a certain pattern (generally is a fish bond) is formed on the lower side of the substrate. Particularly, the surfaces of the two substrates do not comprise PI alignment films, and liquid crystal medium is added between the two substrates. The liquid crystal medium comprises liquid crystal vertical alignment agent, liquid crystals, photopolymerization monomer RM wherein the liquid crystal vertical alignment agent is employed to make the liquid crystals vertically orientated on the surfaces of the substrates in an initial state. In condition that the voltage is applied to the liquid crystal element of the display element, with the function of the electrical field, and the LC in various areas falls down toward the preset directions. Then, after irradiation of ultraviolet light to make the photopolymerization monomer RM generate ultraviolet light polymerization to form protruding objects having the LC introduced to fall, which are deposed on the surface of the substrate for the alignment function.

Specifically, the liquid crystal vertical alignment agent used in the embodiment of the present invention will not have polycondensation to be polysilane. Because the liquid crystal vertical alignment agent is fixed on the surface of the substrate with the head group, namely, the UV light irradiates the liquid crystal vertical alignment agent containing double bond group, the liquid crystal vertical alignment agent cannot move, and the polycondensation to form polysilane is impossible.

In the embodiment of the present invention, the liquid crystals are nematic liquid crystals.

In the preferred embodiment of the present invention, the liquid crystals are dielectric anisotropic nematic liquid crystals. Specifically, Dicyanobenzene liquid crystal, pyridazinone liquid crystal, Schiffs base liquid crystal, azoxy liquid crystal, biphenyls liquid crystal, Phenylcyclohexane liquid crystal, Pyrimidine liquid crystal, Dioxane liquid crystal, bicyclo-octanes liquid crystal, cubane liquid crystal can be employed.

In the embodiment of the present invention, a mass ratio of the liquid crystal vertical alignment agent in the liquid crystal medium is 0.1%-5%.

In the embodiment of the present invention, a mass ratio of the photopolymerization monomer RM in the liquid crystal medium is 0.01%-0.1%.

In the embodiment of the present invention, the photopolymerization monomer RM is

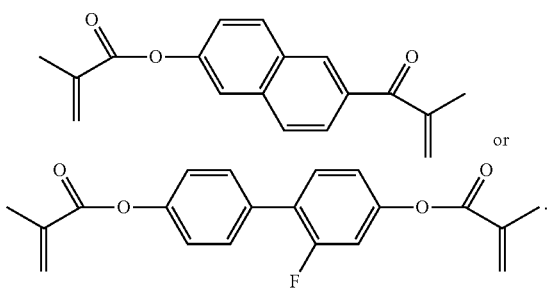

The substrate can be common substrate in the liquid crystal display technology field as long as it is a highly transparent substrate without any particular restriction. Preferably, transparent electrodes employed for driving liquid crystal are formed on the substrate.

As being the specific embodiments, the substrates, the glass plate or plastic substrate such as, Poly Bisphenol A carbonate, Poly Methyl Acrylate, Polyethylene, Polyester, Polyurethane, Polysulfone, Polyether, Polyetherketone, Trimethylpentene, Polyolefin, Polyethylene terephthalate, Methacrylonitrile cellulose acetate butyrate, formed with the transparent electrodes thereon can be illustrated.

Preferably, the substrate with 1-10 μm strip/slit electrode pattern formed on one side thereof and no structure of slit pattern or protruding pattern formed on the opposite side thereof is preferably employed. With the liquid crystal display element substrate of such structure, the steps of manufacture can be simplified and the high transmission ratio can be obtained.

Besides, in the TFT-LCD, the color filter substrate (i.e. CF substrate) and the array substrate (TFT substrate) can be employed to be the substrates.

AS being the transparent electrode located on one side of the substrate (or the transparent conductive film), the ITO manufactured with the indium oxide-stannic oxide ($In_2O_3-SnO_2$), the conductive film manufactured with the stannic oxide ($SnO_2$).

In the liquid crystal display element precursor after the liquid medium is injected, the liquid crystal molecules are vertically aligned on the surface of the substrate. After applying voltages to the electrodes of the two substrates of the liquid crystal display element precursor, and irradiating with ultraviolet light, the RM generates polyreaction to obtain the liquid crystal display element.

The applying voltage is 10-20V. The high-voltage mercury lamp, ultra high-voltage mercury lamp, the metal halide lamp and etc. are employed to implement the irradiation of ultraviolet light. The irradiation volume is 0.01-1 $mW/cm^2$ (in condition of 313 nm wavelength), and preferable to be 0.5 $mW/cm^2$; the UV irradiation period is preferably to be 80-100 s, and then, after the voltage is removed, the UV light of 0.03 $mW/cm^2$ is utilized to irradiate for 100-120 min.

Before the liquid crystal display element provided by the present invention is applied with voltages and irradiated with ultraviolet light, the liquid crystal vertical alignment agent is employed to make the liquid crystals vertically orientated on the surfaces of the substrates in an initial state. The initial alignment directions of the whole liquid crystals are more consistent. After an appropriate voltage is applied thereto, the liquid crystal molecules will be twisted. Then, after irradiation of ultraviolet light with a certain energy to make the RM be polymerized and deposed on the surface of the substrate, the objective of anchoring liquid crystals LC can be realized; after the applied voltage is removed, the LC molecules can generate a certain twisted angle to obtain the liquid crystal display element.

Specifically, the liquid crystal vertical alignment agent makes the liquid crystal molecules vertically orientated on the surfaces of the substrates. When the liquid crystal vertical alignment agent contains unsaturated bond, such as double bond or triple bond, under the irradiation of ultraviolet light, the RM will generates polymerization with the liquid crystal vertical alignment agent to create the polymer network. The liquid crystal molecules around the polymer network will be anchored in advance; when the liquid crystal vertical alignment agent does not contain double bond, under the irradiation of ultraviolet light, the RM containing double bonds generates polymerization to create the polymer network so that the liquid crystal generates a twisted angle and the response speed is raised.

The liquid crystal display element provided by the present invention utilizes the said liquid crystal vertical alignment agent to make the alignment of the liquid crystal molecules in the vertical direction more consistent and have long term stability. Thus, the response speed of the liquid crystal display element is faster to show the great electrical property, transmission and contrast. The image display performance is excellent.

Third, the present invention provides a manufacture method of a liquid crystal display element, comprising steps of:

(1) adding a liquid crystal vertical alignment agent in liquid crystals containing a photopolymerization monomer to obtain a liquid crystal medium, and a molecular formula of the vertical alignment agent is represented by $R_2Si$—$(OR_1)_3$, wherein $R_1$ is —$Si(CH_3)_3$, an alkyl group of which a number of H atom or carbon atom is 1-5, and $R_2$ is a structure of the following equation (E):

$$-B_1-B_2-B_3-B_4-C \qquad (E),$$

in equation (E), $B_1$ is single chain, —$CH_2$— or —$(CH_2)_2$—, $B_2$ is —O—, —COO—*, —OCO—* or —NHCO—*, wherein the * of $B_2$ is linked at one side of $B_3$, and $B_3$ is phenylene, alkylene of which a number of carbon atoms is 2-6, alkylene containing olefinic bond or acetylene bond of which a number of carbon atoms is 3-8, and $B_4$ is —O—, —(CO)NH—*, —COO—* or —OCO—*, wherein the * of $B_4$ is linked at one side of C, and C is linear alkylbenzene of which a number of carbon atoms is 1-10;

(2) adding the aforesaid liquid crystal medium between two substrates, which are oppositely positioned and have conductive films to obtain a liquid crystal display element precursor, wherein surfaces of the substrates do not comprises liquid crystal alignment films;

(3) irradiating the liquid crystal display element precursor with ultraviolet light to form the liquid crystal display element in a state of being applied with voltages.

In the embodiment of the present invention, $R_1$ is linear alkyl or branched alkyl of which a number of carbon atoms is 1-5.

In the embodiment of the present invention, $R_1$ is —$CH_3$, —$Si(CH_3)_3$ or —$CH_2CH_3$.

In the embodiment of the present invention, the $B_3$ is —$C_6H_4$—, liner alkylidene radical of which a number of carbon atoms is 2-6, —CH═CH— or —$(CH_3)C$═C$(CH_3)$—.

In the preferred embodiment of the present invention, the C is linear alkylbenzene of which a number of carbon atoms is 5-8.

In the embodiment of the present invention, a mass ratio of the liquid crystal vertical alignment agent in the liquid crystal medium is 0.1%-5%.

In the embodiment of the present invention, a mass ratio of mass sum of the photopolymerization monomer RM in the liquid crystal medium and the photopolymerization monomer is 0.01%-0.1%.

In the embodiment of the present invention, the photopolymerization monomer RM is

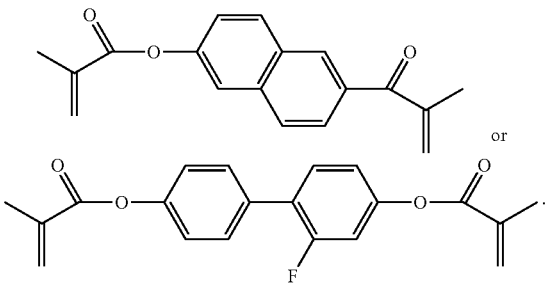

With the well known method, the liquid crystal display element of the present invention can be obtained. Generally, a pair of substrates without liquid crystal alignment films is oppositely positioned with spacers, and the peripheral parts of the two substrates are attached with sealant. Then, the liquid crystal medium is injected into the cell gaps divided with the surfaces of substrates and the sealant, and the injection hole is closed to construct the cell. Then, polarizers are located at the outer sides of the respective substrate constructing the cell box to manufacture the liquid crystal display element.

As being the sealant, the epoxy resin to be the hardening agent and the separator of the alumina ball can be illustrated.

No particular restriction are to the method of injecting liquid crystal medium between the substrates. As illustrations, here are the vacuum methods of liquid crystal injection, the drop method of implementing seal after the liquid crystal is dropped, and etc. after the manufactured liquid crystal display element precursor is decompressed.

In the embodiment of the present invention, the liquid crystal medium is injected between the substrates having conductive films with a one drop filling (ODF) process.

Specifically, the aforesaid liquid crystal medium containing the vertical alignment agent and the frame glue are dropped on the array substrate or on the color filter substrate in order. Then, array substrate and the color filter substrate are laminated in vacuum condition with accuracy range of several micrometers. After the lamination is accomplished, the heat curing process is implemented after the UV light irradiation to the frame glue. Then, the liquid crystal molecules are vertically aligned on the surface of the substrate with the function of the vertical alignment agent, and by applying voltages to the electrodes of the two substrates, the polyreaction occurs between the RMs or between the RM and the liquid crystal vertical alignment agent under the irradiation of UV light.

The applying voltage is 10-20V. The high-voltage mercury lamp, ultra high-voltage mercury lamp, the metal halide lamp and etc. are employed to implement the irradiation of ultraviolet light. The irradiation volume is 0.01-1 mW/cm²J (in condition of 313 nm wavelength), and preferable to be 0.5 mW/cm$^2$; the UV irradiation period is preferably to be 80-120 s, and then, after the voltage is removed, the UV light of 0.03 mW/cm$^2$ is utilized to irradiate for 100-120 min.

The manufacture method of the liquid crystal display element provided by the embodiment of the present invention makes the manufacture process simple, and strong operation operability to replace the manufacture of the alignment film such as polyimide (PI) in the thin film transistor LCD (TFT-LCD). It can significantly simplifies the manufacture flow of the liquid crystal display element to reduce the production cost of the liquid crystal display element, and raise the display performance of the liquid crystal display element.

Embodiment One

A manufacture method of a liquid crystal display element, comprising steps of:

(1) adding a liquid crystal vertical alignment agent in liquid crystals (LC) containing a photopolymerization monomer RM to obtain a liquid crystal medium, wherein a mass ratio of the liquid crystal vertical alignment agent in the liquid crystal medium is 1%, and a mass ratio of the photopolymerization monomer RM in the liquid crystal medium is 0.05%, and a constitutional formula of the photopolymerization monomer RM is

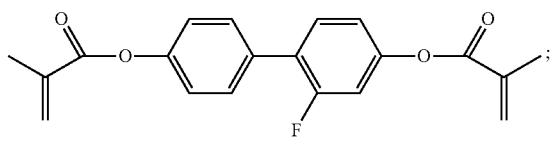

(2) drop adding the aforesaid liquid crystal medium on the TFT substrate having the ITO conductive film with ODF process, and oppositely positioning the substrate with another color filter substrate (CF substrate) having the ITO conductive film, and attaching the peripheral parts of the two substrates with sealant to obtain a liquid crystal display element precursor, wherein the substrates do not comprises liquid crystal alignment films;

(3) applying a voltage of 19V to the electrodes of the two substrates of the liquid crystal display element precursor, and in condition of applying the voltage of 19V, irradiating the liquid crystal display element precursor with ultraviolet light for 100 s, and the energy of the ultraviolet light is 0.5 mW/cm$_2$, and after the voltage is removed, the UV light of 0.03 mW/cm$_2$ is utilized to irradiate for 120 min to form the liquid crystal display element TFT-LCD.

In the step (1), the structure diagram of the liquid crystal vertical alignment agent can be represented by FIG. 1, wherein A represents the head group Si(OSi(CH$_3$)$_3$)$_3$—, the middle base group B is —O—(CH$_2$)$_6$—O—, and the tail group C is an alkyl group of which a number of carbon atom is 6.

In the step (2), the TFT substrate comprises a SiNx protective film and an ITO conductive film (or so called ITO electrode). The TFT substrate at lower side comprises the ITO electrode with a certain pattern (generally is a fish bond).

As described in the present invention, in the step (2), the CF substrate comprises an ITO conductive film (or so called ITO electrode). The upper layer, C substrate comprises an ITO electrode on the entire surface.

As described in the present invention, the surfaces of the TFT substrate, the CF substrate do not comprise PI alignment films.

Figure 2:
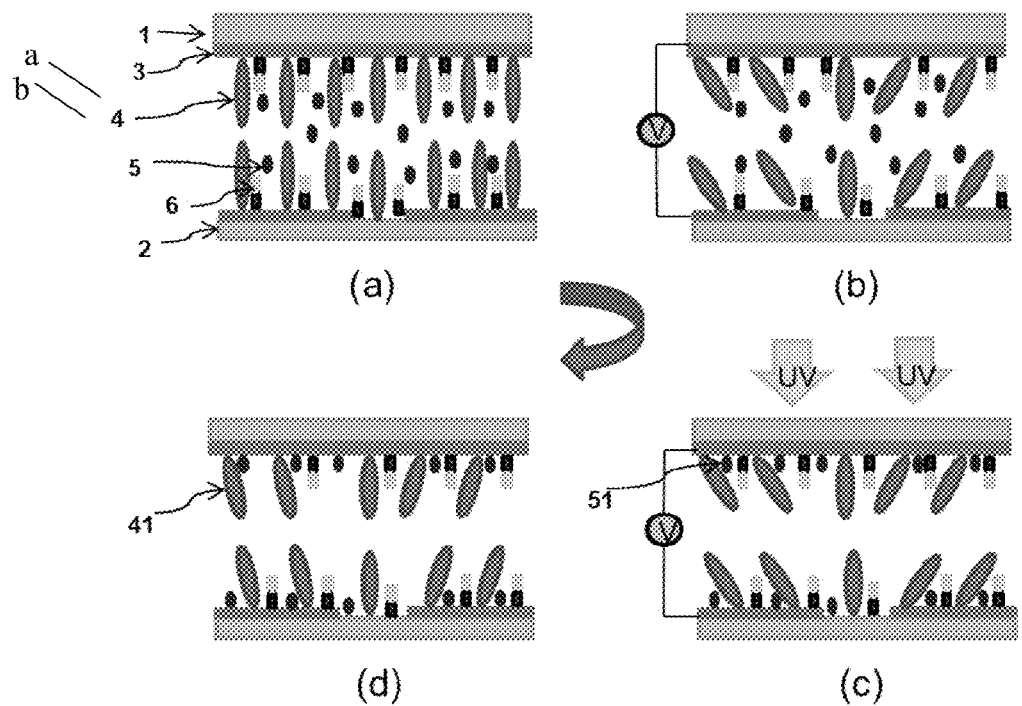
FIG. 2 is a manufacture process diagram of the liquid display element in the embodiment of the present invention, wherein 1 is CF substrate, of which an ITO electrode 3 is on the entire surface, and the substrate 2 of the other side is a TFT substrate, of which an ITO electrode of certain pattern is on the surface, and 4 is liquid crystal, 5 is the photopolymerization monomer, 6 is the liquid crystal vertical alignment agent, 51 is polymer formed by the photopolymerization monomer, and 41 is liquid crystal formed with having a pre-tilted angle.

In the step (2), in an initial state with the function of the liquid crystal vertical alignment agent, the LC molecules are vertically aligned on the surface of the substrate (as shown in FIG. 2(a)).

In the step (3), after applying voltages to the electrodes of the two substrates of the liquid crystal display element precursor, the liquid crystal molecules in various areas are twisted (as shown in FIG. 2(b)) with the function of the electrical field, and the LC falls down toward the preset direction; with irradiating with ultraviolet light, the RM generates light polyreaction to form polymer having the LC introduced to fall, which is deposed on the surface of the substrate for anchoring the LC molecules (as shown in FIG. 2(c)); finally, the applying voltage is removed, the LC molecule generates a twisted angle (as shown in FIG. 2(d)) and ultimately, the liquid crystal display element is obtained.

Embodiment Two

A manufacture method of a liquid crystal display element, comprising steps of:

(1) adding a liquid crystal vertical alignment agent shown in formula (III) in liquid crystals (LC) containing a photopolymerization monomer RM to obtain a liquid crystal medium, wherein a mass ratio of the liquid crystal vertical alignment agent in the liquid crystal medium is 0.1%, and a mass ratio of the photopolymerization monomer RM in the liquid crystal medium is 0.01%, and a constitutional formula of the photopolymerization monomer RM is

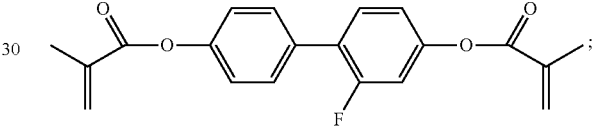

(2) drop adding the aforesaid liquid crystal medium between the TFT-LCD substrates (the same TFT substrate, CF substrate in the embodiment 1) having the ITO conductive films with ODF to obtain a liquid crystal display element precursor, and the two substrates of the TFT-LCD do not comprises liquid crystal alignment films;

(3) applying a voltage of 19V to the electrodes of the two substrates of the liquid crystal display element precursor, and irradiating the liquid crystal display element precursor with ultraviolet light for 80 s, and the energy of the ultraviolet light is 1 mW/cm$^2$, and after the voltage is removed, the UV light of 0.03 mW/cm$^2$ is utilized to irradiate for 110 min to form the liquid crystal display element TFT-LCD.

Embodiment Three

A manufacture method of a liquid crystal display element, comprising steps of:

(1) adding a liquid crystal vertical alignment agent shown in formula (VI) in liquid crystals (LC) containing a photopolymerization monomer RM to obtain a liquid crystal medium, wherein a mass ratio of the liquid crystal vertical alignment agent in the liquid crystal medium is 1%, and a mass ratio of the photopolymerization monomer RM in the liquid crystal medium is 0.1%, and a constitutional formula of the photopolymerization monomer RM is

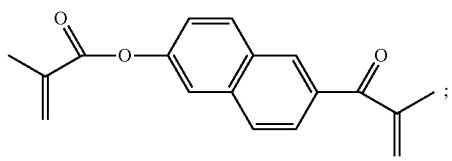 [SMILES: C=C(C)C(=O)Oc1ccc2cc(C(=O)C(=C)C)ccc2c1]

(2) drop adding the aforesaid liquid crystal medium on the TFT substrate having the ITO conductive film with ODF, and oppositely positioning the substrate with another color filter substrate (i.e. the CF substrate) having the ITO conductive film, and attaching the peripheral parts of the two substrates with sealant to obtain a liquid crystal display element precursor, and the substrates do not comprises liquid crystal alignment films;

(3) applying a voltage of 19V to the electrodes of the two substrates of the liquid crystal display element precursor, and in condition of applying the voltage of 19V, irradiating the liquid crystal display element precursor with ultraviolet light for 120 s, and the energy of the ultraviolet light is 0.01 mW/cm$^2$, and after the voltage is removed, the UV light of 0.03 mW/cm$^2$ is utilized to irradiate for 110 min to form the liquid crystal display element TFT-LCD.

The above-described embodiment is merely the expression of several embodiments of the present invention, the description is more specific and detailed, but it cannot be construed as limiting the scope of the invention. It should be noted that any persons who are skilled in the art change or replacement which is easily derived should be covered by the protected scope of the invention. Thus, the protected scope of the invention should go by the subject claims. Accordingly, the scope of the present invention patent protection should prevail in the appended claims.

What is claimed is:

1. A liquid crystal vertical alignment agent, and a molecular formula of the liquid crystal vertical alignment agent is represented by $R_2Si$—$(OR_1)_3$, wherein $R_1$ is —$Si(CH_3)_3$, or an alkyl group of which a number of carbon atom is 1-5, and $R_2$ is a structure of the following equation (E):

—$B_1$—$B_2$—$B_3$—$B_4$—C            (E), in equation (E), $B_1$ is a linear organic group, $CH_2$— or —$(CH_2)_2$—, $B_2$ is —O—, —COO—*, —OCO—* or —NHCO—*, in which wherein the * of $B_2$ is linked at one side of $B_3$; $B_3$ is phenylene, an alkylene of which a number of carbon atoms is 2-6, or an alkylene containing olefinic bond or acetylene bond of which a number of carbon atoms is 3-8; $B_4$ is —O—, —(CO)NH—*, —OCO—* or —OCO—*, in which the * of $B_4$ is linked at one side of C, and C is a linear alkylbenzene of which a number of carbon atoms is 7-10.

2. The liquid crystal vertical alignment agent according to claim 1, wherein the $R_1$ is —$CH_3$, —$Si(CH_3)_3$ or —$CH_2CH_3$.

3. The liquid crystal vertical alignment agent according to claim 1, wherein the $B_3$ is —$C_6H_4$—, liner alkylidene radical of which a number of carbon atoms is 2-6, —CH═CH— or —$(CH_3)C$═$C(CH_3)$—.

4. The liquid crystal vertical alignment agent according to claim 1, wherein the C is linear alkylbenzene of which a number of carbon atoms is 7-8.

5. A liquid crystal display element, comprising a liquid crystal display element precursor; wherein the liquid crystal display element precursor comprises two substrates, which are oppositely positioned and have conductive films, and a liquid crystal medium positioned between the substrates; wherein the liquid crystal medium comprises a liquid crystal vertical alignment agent, liquid crystals and a photopolymerization monomer, wherein surfaces of the substrates do not comprise liquid crystal alignment films, and the liquid crystal vertical alignment agent is employed to make the liquid crystals vertically orientated on the surfaces of the substrates in an initial state; the liquid crystal display element precursor is employed to be irradiated with ultraviolet light to form the liquid crystal display element in a state of being applied with voltages, wherein a molecular formula of the liquid crystal vertical alignment agent is represented by $R_2Si$—$(OR_1)_3$, and R1 is —$Si(CH_3)_3$, or an alkyl group of which a number of carbon atom is 1-5, and $R_2$ is a structure of the following equation (E):

—$B_1$—$B_2$—$B_3$—$B_4$—C            (E), in equation (E), $B_1$ is a linear organic group, —$CH_2$— or —$(CH_2)_2$—, $B_2$ is —O—, —COO—*, —OCO—* or —NHCO—*, in which the * of $B_2$ is linked at one side of $B_3$; $B_3$ is phenylene, an alkylene of which a number of carbon atoms is 2-6, or an alkylene containing olefinic bond or acetylene bond of which a number of carbon atoms is 3-8; $B_4$ is —O—, —(CO)NH—*, —OCO—* or —OCO—*, in which the * of $B_4$ is linked at one side of C, and C is a linear alkylbenzene of which a number of carbon atoms is 7-10.

6. The liquid crystal display element according to claim 5, wherein a mass ratio of the liquid crystal vertical alignment agent in the liquid crystal medium is 0.1%-5% of a total mass of the liquid crystal medium.

7. The liquid crystal display element according to claim 5, wherein a mass ratio of the photopolymerization monomer in the liquid crystal medium is 0.01%-0.1% of a total mass of the liquid crystal medium.

8. The liquid crystal display element according to claim 5, wherein the photopolymerization monomer is

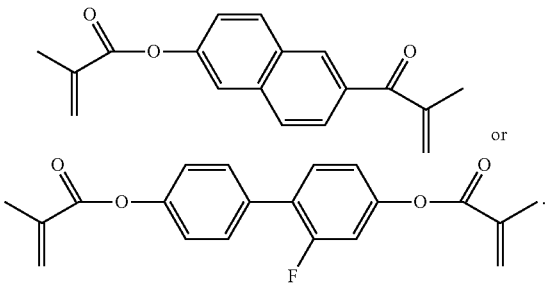

9. A manufacture method of a liquid crystal display element, comprising steps of:

(1) adding a liquid crystal vertical alignment agent in liquid crystals containing a photopolymerization monomer to obtain a liquid crystal medium, and a molecular formula of the vertical alignment agent is represented by $R_2Si$—$(OR_1)_3$, wherein $R_1$ is —$Si(CH_3)_3$, or an alkyl group of which a number of H atom or carbon atom is 1-5, and $R_2$ is a structure of the following equation (E):

—$B_1$—$B_2$—$B_3$—$B_4$—C            (E), in equation (E), $B_1$ is a linear organic group, $CH_2$— or —$(CH_2)_2$—, $B_2$ is —O—, —COO—*, —OCO—* or —NHCO—*, in which the * of $B_2$ is linked at one side of $B_3$; $B_3$ is phenylene, an alkylene of which a number of carbon atoms is 2-6, or an alkylene containing olefinic bond or acetylene bond of which a number of carbon atoms is 3-8; $B_4$ is —O—, —(CO)NH—*, —OCO—* or —OCO—*, in which the * of $B_4$ is linked at one side of C, and C is a linear alkylbenzene of which a number of carbon atoms is 7-10;

(2) adding the aforesaid liquid crystal medium between two substrates, which are oppositely positioned and have conductive films to obtain a liquid crystal display element precursor, wherein surfaces of the substrates do not comprises liquid crystal alignment films;

(3) irradiating the liquid crystal display element precursor with ultraviolet light to form the liquid crystal display element in a state of being applied with voltages.

10. The manufacture method of the liquid crystal display element according to claim 9, wherein in the step (2), the liquid crystal medium is injected between the substrates having conductive films with a one drop filling process.

\* \* \* \* \*